(12) United States Patent
Whalen

(10) Patent No.: US 6,685,974 B2
(45) Date of Patent: *Feb. 3, 2004

(54) PROCESS FOR PREPARING AN OAT-BASED FUNCTIONAL SYRUP

(75) Inventor: Paul J. Whalen, Elk River, MN (US)

(73) Assignee: American Oats, Inc., Minneapolis, MN (US)

(*) Notice: Subject to any disclaimer, the term of this patent is extended or adjusted under 35 U.S.C. 154(b) by 226 days.

This patent is subject to a terminal disclaimer.

(21) Appl. No.: 09/878,769

(22) Filed: Jun. 11, 2001

(65) Prior Publication Data

US 2002/0018830 A1 Feb. 14, 2002

Related U.S. Application Data

(63) Continuation-in-part of application No. 09/414,216, filed on Oct. 7, 1999, now Pat. No. 6,395,314, which is a division of application No. 09/033,375, filed on Mar. 2, 1998, now Pat. No. 5,989,598, which is a continuation-in-part of application No. 08/591,863, filed on Jan. 25, 1996, now Pat. No. 5,723,162, which is a continuation-in-part of application No. 08/379,398, filed on Jan. 26, 1995, now abandoned.

(51) Int. Cl.[7] .............................................. A23L 1/076
(52) U.S. Cl. ........................... 426/52; 426/28; 426/253; 426/524; 426/549; 426/590; 426/599; 426/618; 426/639
(58) Field of Search ............................. 426/52, 28, 590, 426/599, 253, 549, 618, 639, 524

(56) References Cited

U.S. PATENT DOCUMENTS

| | | | |
|---|---|---|---|
| 3,644,126 A | 2/1972 | Bodnar et al. ............... 99/142 |
| 4,199,605 A | 4/1980 | Kahn et al. ............... 426/330.6 |
| 4,244,981 A | 1/1981 | Blake ........................ 426/567 |
| 4,311,714 A | 1/1982 | Goering et al. ............... 426/28 |
| 4,335,155 A | 6/1982 | Blake et al. ................ 426/565 |
| 4,374,860 A | 2/1983 | Gasser et al. ................. 426/28 |
| 4,428,967 A | 1/1984 | Goering et al. ............... 426/28 |
| 4,510,166 A | 4/1985 | Lenchin et al. ............. 426/565 |
| 4,744,992 A | 5/1988 | Mitchell et al. .............. 426/29 |
| 4,804,545 A | 2/1989 | Goering et al. ............... 426/28 |
| 4,871,571 A | 10/1989 | Jensen et al. ............... 426/548 |
| 4,894,242 A | 1/1990 | Mitchell et al. .............. 426/29 |
| 4,908,223 A | 3/1990 | Murtaugh .................... 426/565 |
| 4,948,614 A | 8/1990 | Feldpausch ................. 426/565 |

(List continued on next page.)

FOREIGN PATENT DOCUMENTS

| | | |
|---|---|---|
| EP | 0 031 050 | 11/1980 |
| EP | 0 487 187 A1 | 8/1991 |
| EP | 0 486 936 A1 | 11/1991 |
| EP | 0 540 421 A1 | 10/1992 |
| WO | 95/07628 | 3/1995 |
| WO | 95/10196 | 4/1995 |

OTHER PUBLICATIONS

Janet Raloff, Beyond Oat Bran–Reaping the benefits without gorging on the grain, beginning on page 62 (3 pages) of Food Technology.

Elizabeth Bertini, Make Room for Oat Milk, P. 72 of National Foods Merchandise.

Novo Indsti A/S Enzymes Division, Novo's Handbook of Practical Biotechnology, 1986 pp. 35–41.

*Primary Examiner*—Helen Pratt
(74) *Attorney, Agent, or Firm*—Patterson, Thuente, Skaar & Christensen, P.A.

(57) ABSTRACT

A process for preparing an oat-based functional syrup. The process includes milling an oat material to produce a base formulation. Material having a granulation of more than U.S. #100 mesh is separated from the base formulation. The base formulation is then blended with water to form a slurry. Effective amounts of alpha-amylase enzyme and glucoamylase enzyme are mixed into the slurry. The slurry is then cooked to convert the slurry into a syrup. The syrup is substantially flavorless.

27 Claims, 1 Drawing Sheet

U.S. PATENT DOCUMENTS

| | | |
|---|---|---|
| 4,954,360 A | 9/1990 | Barnett ....................... 426/565 |
| 4,990,344 A | 2/1991 | Euber et al. ................... 426/28 |
| 4,996,063 A | 2/1991 | Inglett ......................... 426/21 |
| 5,013,561 A | 5/1991 | Goering et al. ............... 426/28 |
| 5,082,673 A | 1/1992 | Inglett ......................... 426/21 |
| 5,110,612 A | 5/1992 | Quarles et al. ............. 426/548 |
| 5,234,704 A | 8/1993 | Devine et al. ............... 426/565 |
| RE34,508 E | 1/1994 | Murtaugh et al. ........... 426/565 |
| 5,393,550 A | 2/1995 | Tarr et al. .................... 426/573 |
| 5,407,694 A | 4/1995 | Devine et al. ............... 426/565 |
| 5,468,491 A * | 11/1995 | Targan ......................... 426/29 |

* cited by examiner

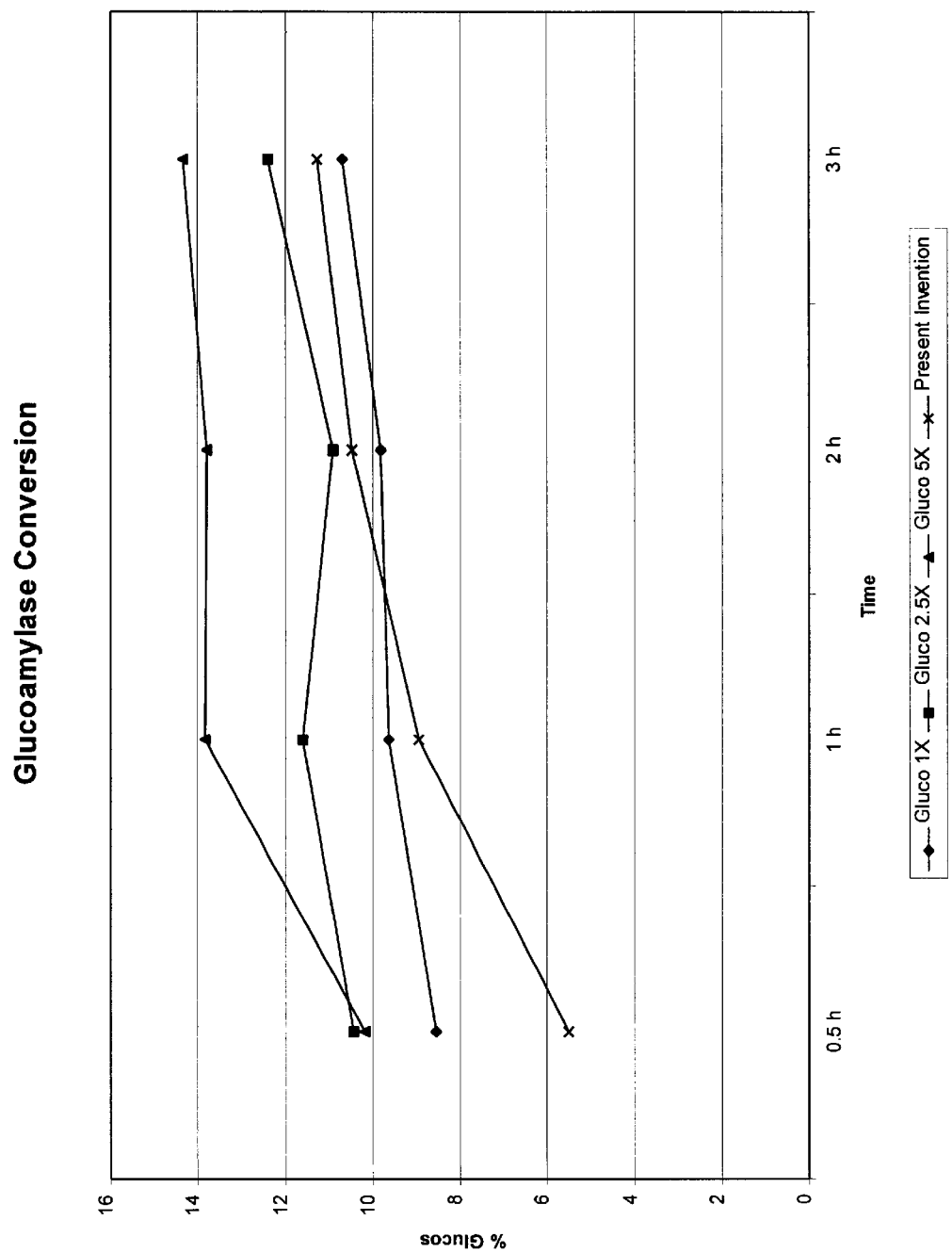

PROCESS FOR PREPARING AN OAT-BASED FUNCTIONAL SYRUP

RELATED U.S. APPLICATION DATA

This application is a continuation-in-part of application Ser. No. 09/414,216, filed Oct. 7, 1999, now U.S. Pat. No. 6,395,314 which is a divisional of application Ser. No. 09/033,375, filed Mar. 2, 1998, now U.S. Pat. No. 5,989,598, which is a continuation-in-part of application Ser. No. 08/591,863, filed Jan. 25, 1996, now U.S. Pat. No. 5,723,162, which is a continuation-in-part of application Ser. No. 08/379,398, filed Jan. 26, 1995, now abandoned.

FIELD OF THE INVENTION

The present invention relates generally to food products and beverages. More particularly, the present invention relates to an oat-based functional syrup that is used in food products.

BACKGROUND OF THE INVENTION

Consumers are increasingly concerned about purchasing and consuming products that the consumers view as being more healthful. For example, products possessing higher levels of complex carbohydrates and fiber, especially soluble fiber, are becoming more popular with consumers. In addition, products containing lower levels of fat and cholesterol as well as a decreased caloric content are becoming more popular with consumers. Many consumers also desire products made from all-natural components that contain no stabilizers, emulsifiers, or other exogenous additives, such as refined sugars or artificial sweeteners.

Non-dairy sweet confections are becoming popular alternatives to conventional dairy-based frozen confections. Consumers who are lactose intolerant are especially interested in purchasing products that do not contain dairy products or dairy derivatives.

One drawback of products produced for the health conscious market is that they tend to be less sweet than conventional dairy-based frozen desserts. This problem has been overcome by the addition of various sweeteners, such as sucrose, glucose syrup, and high fructose corn syrup. While these products may appeal to some segments of the health conscious market, these products are not desired by consumers who exclude refined or artificial sweeteners from their diet.

A variety of non-dairy compositions have been developed that appeal to the various segments of the health conscious market. Unfortunately, none of the products deliver all of the benefits of being lactose free, high in soluble fiber, free of exogenous additives, and sweet without the addition of refined sugars and artificial sweeteners. A product that delivers all these benefits would be acceptable as a substitute for dairy-based products even by consumers who are not interested in the health benefits of such a product.

An article by Janet Raloff (*Beyond Oat Bran*, Food Technology 1991 vol. 8, page 62) describes the physiological benefits of consuming an oat-based product, which is identified by the name Oatrim. The oat-based product is formulated from either oat bran or oat flour. The article indicates that the odorless and nearly tasteless oat-based product is particularly suited as a fat replacement in low-temperature applications, such as frozen confections.

The oat-based product is described in further detail in Inglett, U.S. Pat. Nos. 4,996,063 and 5,082,673. A mixture of oats and water is gelatinized by passage through a steam injection cooker at a temperature of between 138° C. and 143° C. After the pH of the mixture is adjusted, alpha-amylase enzymes are added to hydrolyze the starch in the mixture. Once hydrolyzation is complete, soluble fiber is separated from the mixture. Finally, the soluble fiber is dehydrated to provide the oat-based product. Examples in the Inglett patents indicate that the oat-based product is mixed with additional components, such as milk and sugar, to formulate the frozen confection.

Mitchell et al., U.S. Pat. No. 4,744,992, discloses using a dual enzyme method, which includes liquefying and saccharifying rice, to produce a high glucose syrup. Examples in the Mitchell et al. patent indicate that when the syrup is incorporated into a frozen confection, vegetable oil in a concentration of approximately 10 percent by weight of the frozen confection as well as stabilizers are added to provide the frozen confection with a creamy texture. Mitchell et al. also indicates that liquefaction is performed at a temperature of approximately 80° C.

Murtaugh et al., U.S. Pat. No 4,908,223, discloses an oat- or rice-based frozen confection and a method of preparing the frozen confection. Murtaugh et al. describes cooking an aqueous mixture of oats or rice. After the cooking is complete, liquefying, sweetening, and flavoring agents are added to the mixture so that the frozen confection exhibits ice cream-like characteristics.

Murtaugh et al., U.S. Pat. No. 4,908,223, discloses an oat or rice-based frozen confection and a method of preparation. Murtaugh et al. describes that refined sweeteners are added to improve the functional and organoleptic properties of the product. Murtaugh et al. does not rely on the syrup to provide the product with a desirable taste but rather adds other components such as fruit and sugar to enhance the taste of the final product.

Reinl et al., U.S. Pat. No. 4,857,356, also addresses enzymatic processing of grain. Reinl et al. indicates that liquefaction is performed at a temperature of between about 130 and 160° C. Similar to Murtaugh et al., Reinl et al. relies on additives such as fruit comprising 50 percent or more of the cereal base to make the produce more palatable rather than the flavor of the syrup.

Several fruit-based frozen confections have also been developed. For example, Feldpausch, U.S. Pat. No. 4,948,614, describes using bananas to produce a non-dairy confection. Blake et al., U.S. Pat. No. 4,335,155, discloses that any fruit, which can be made into a puree, is suitable for use as a base of a frozen confection. Blake, U.S. Pat. No. 4,244,981, describes using citrus juice vesicles as the primary component of a frozen confection.

SUMMARY OF THE INVENTION

The present invention includes a process for preparing an oat-based functional syrup. The process includes milling an oat material to produce a base formulation. Material having a granulation of more than U.S. #100 mesh is separated from the base formulation. The base formulation with water is then blended to form a slurry. Next, effective amounts of alpha-amylase enzyme and glucoamylase enzyme are mixed into the slurry. The slurry is then cooked to convert the slurry into a syrup. The syrup is substantially flavorless.

BRIEF DESCRIPTION OF THE DRAWINGS

FIG. 1 is a graph of glucoamylase conversion rates.

DETAILED DESCRIPTION OF THE PREFERRED EMBODIMENTS

The present invention includes an oat-based functional syrup and a process for forming the oat-based functional syrup. The use of the term functional in the name of the product of the present invention indicates that the oat-based functional syrup has certain characteristics that make this product useful in fabricating food products and beverages.

The oat-based functional syrup of the present invention has several advantages over prior art syrup bases. The oat syrup of the present invention is substantially flavorless. The oat syrup of the present invention also has a nearly white color. Additionally, the oat syrup exhibits desirable sweetness, texture, and mouthfeel characteristics when formed into a non-dairy frozen confection without exogenous sweeteners, stabilizers, emulsifiers, or proteins, which are commonly used in prior art non-dairy frozen confections. As used herein, the term "mouthfeel" refers to a creamy sensation that a person experiences in one's mouth upon consuming ice cream. As used herein, the term "exogenous" refers to components that are added to prior art food products and beverages to supplement or modify the characteristics of the prior art food products and beverages.

Frozen confections made from prior art syrup products typically require emulsification and homogenization to produce characteristics that are commonly associated with dairy-based frozen confections. When producing the food products and beverages, the oat-based functional syrup does not require emulsification or homogenization.

The properties of the oat-based functional syrup are dictated by the particular oat or grain components selected. It has been found that using a low bran flour, which is substantially reduced in bran while retaining soluble fiber glucans, provides the food products and beverages with desired characteristics. The term "bran," as used herein, refers to the dark fibrous component found in ground oat flour. The typical compositional analysis of low bran oat flour is similar to whole oat flour for moisture, protein, and fat, as illustrated in Table 1.

TABLE 1

| Composition (weight percent) | Whole Oat Flour | Low Bran Oat Flour | Fine Oat Flour |
| --- | --- | --- | --- |
| Moisture | 11 | 11 | 10 |
| Protein | 18 | 15 | 10 |
| Fat | 7 | 7 | 6 |
| Total Dietary Fiber | 9 | 10 | 4–7 |
| Beta-Glucan | 4 | 7 | 2–4 |

While it is also possible to use oats or grains having a significant hull, bran, or husk portion to formulate the syrup, syrup formed from these materials must be separated from insoluble branny particles present in the syrup before the food product or beverage is produced from the syrup. As an alternative to using the oats in the form of flour, it is also possible to practice the present invention with other forms of oats, such as rolled oats, partially milled oats, and oatmeal. These various forms of oats are collectively identified as "oat material".

One particular oat flour possessing a low level of bran or hull material is fine oat flour. Fine oat flour is a fraction of the whole oat flour obtained from a sieving or air classification process.

The typical compositional analysis of fine oat flour is similar to whole oat flour for moisture, protein, and fat, as illustrated in Table 1. Fine oat flour also retains a substantial percentage of the soluble fiber that is present in whole oat flour. However, fine oat flour contains less bran or insoluble fiber and more starch than whole oat flour.

The various fractions formed in the oat milling stream produce food products and beverages with varied characteristics. The fractions high in soluble fiber, including whole oat flour and oatmeal, tend to give very smooth and somewhat "dry" texture to soft-serve frozen dessert, while those higher in starch content tend to provide more sweetness. It will be obvious to those skilled in the art that a desired set of finished product characteristics may be obtained by selecting an appropriate oat starting material or blend of available oat milling fractions. For example, the frozen confection may be formed from a mixture of fine oat flour and whole oat flour. Oat mill products possessing these characteristics can be obtained from various sources including Conagra, Inc (Council Bluffs, Iowa) or Grain Millers (Minneapolis, Minn.).

It has also been found that a waxy barley hybrid flour also provides desirable results when used with the present invention. The waxy barley hybrid is a hull-less barley that is preferably selected from the prowashneupana variety, which can be obtained from Conagra, Inc. (Council Bluff, Iowa). The typical compositional analysis for the prowashneupana waxy barley hybrid is set forth in Table 2.

TABLE 2

| Composition (weight percent) | Waxy Barley Hybrid Flour |
| --- | --- |
| Moisture | 14 |
| Protein | 20 |
| Fat | 7 |
| Total Dietary Fiber | 29 |
| Beta-Glucan | 14 |

Other starch sources can be used in conjunction with the oat flour or waxy barley hybrid flour to adjust the flavor and sweetness of the food products and beverages. While other starch sources may be used in the preparation of the food products and beverages, the other starch sources only represent a minor portion of oat or grain material (up to 49 percent by weight) that is used to prepare the food products and beverages. The oat flour and waxy barley hybrid flour comprise a major portion of the oat or grain material (50 percent by weight or more) that is used to prepare the oat-based functional syrup.

Examples of starch sources that are suitable for use in the present invention include flours, such as corn flour, wheat flour, rice flour, and potato flour. It is believed that the addition of other starch sources to the oat flour or waxy barley hybrid flour does not affect the functional properties of the food products and beverages, such as texture and mouthfeel characteristics, associated with ice cream-like qualities when a non-dairy frozen confection is prepared from the oat-based functional syrup.

As a preliminary step in the preparation of the oat-based functional syrup, the oat flour or waxy barley hybrid flour is milled to a fine granulation. Next, the ground material is subjected to a separation technique to remove the larger size particles. The separation technique removes substantially all of the ground material that is larger than U.S. #100 mesh and preferably removes substantially all of the ground material that is larger than U.S. #250 mesh.

Since the bran portion of the oat material typically has a particle size that is above this range, a significant portion of the bran portion is removed from the oat material through the separation technique. The separation technique preferably reduces the concentration of the bran component by at least 30 percent by weight and preferably more than 50 percent by weight.

The presence of the bran causes the syrup and subsequent products made from the syrup to be darker in color. In products such as an oat milk or oat ice cream this darker color is an obvious defect. Removal of the insoluble fiber results in a lighter colored syrup when cooked by the procedure delineated below. Hence, the color of an oat drink or vanilla oat ice cream is more appealing to consumers and a significant advantage in the market place. Using an oat material with these characteristics also enhances the texture of the syrup product.

Additionally, using an oat material with these characteristics removes the need for a filtration step that was previously required to produce a syrup product with desirable characteristics. This is a major processing advantage since it is far easier to remove and prevent the effects of the bran in the syrup prior to the hydrolysis process. A final filter may be done but it is not a required step, only a quality assurance step.

Separation is preferably performed with sieve screening or air classification. While both sieve screening and air classification result in very small size material, it has been found that sieve screening results in a higher quality product.

The starch sources are mixed with the oat material to prepare a substantially homogeneous base formulation. A person of ordinary skill in the art will appreciate that the oat material and the starch sources may be mixed together before or after the grinding and separating steps.

A slurry is formed by mixing the base formulation into water in an amount that is effective to provide a solids level of between 25 and 33 percent on a dry matter basis. The water is preferably potable tap water that is provided at a traditional faucet temperature of about 10° C.

Changing the solids level allows the sweetness of the oat-based functional syrup to be adjusted. For example, increasing the solids level causes an increase in the starch component, which increases the sweetness of the oat-based functional syrup.

The cook process preferably includes a one-step procedure. The primary advantage of the one-step procedure is a reduction of processing time. Surprisingly, this combined enzyme procedure also results in a thinner syrup and a more rapid sugar formation.

An advantage to our cook process is the minimization of browning products normally formed in cooks containing high reducing sugar. These products are common and form by the well-known Maillard reaction of reducing sugars and protein. When these off-colors are generated, it is necessary to use reaction processes like activated charcoal to reduce the off-color.

The oat slurry or mixture must be cooked at as low a temperature as possible to minimize flavor defects from bran as well as other components of the oat flour (protein, fat, etc.). The cook temperature is between 60° C. and 70° C., preferably between about 65° C. and 70° C. and optimally about 68° C. Using temperatures in excess of this range (i.e., above 70° C.) result in flavor and color defects.

Using glucoamylase in conjunction with alpha-amylase results in an improved thinning or liquefying action. The combined use of glucoamylase and alpha-amylase also produces rapid sugar formation from the oat material. This procedure results in a higher conversion rate to glucose and a savings in processing time. By decreasing the total thermal exposure of the oat base, the formation of off-flavors from remaining bran and other components in the oat flour is reduced.

The fine oat flour is added along with the standard amount of low temperature active alpha-amylase (Genencor SPEZYME LT-75 or Novo BAN) plus an increased amount of glucoamylase that is about twice the conventionally recommended concentration. The enzymes work in conjunction to speed the formation of glucose.

The alpha-amylase enzymes are preferably alpha-1,4-glucan, 4-glucanohydrolase, which is derived from *Bacillus subtilis*. The alpha-amylase enzymes not only produce liquefaction in a random fashion over a broad range of temperatures (65° C. to 92° C.) but also retain its activity when used at temperatures of less than 80° C.

The alpha-amylase enzymes are preferably food grade alpha-amylase enzymes, which can be obtained from Genencor International (Rochester, N.Y.) under the designation SPEZYME LT-75. The SPEZYME LT-75 enzymes are added to the slurry at a rate of between about 0.50 and 1.25 grams per pound of oat material and preferably about 0.75 grams per pound of oat material.

The dextrin is preferably converted into glucose using glucoamylase enzymes. The glucoamylase enzymes are also referred to as fungal 1,4-alpha-D-glucan glucohydrolase, which can be obtained from Genencor International (Rochester, N.Y.) under the designation SPEZYME GA 300. The glucoamylase enzymes are added to the slurry at a rate of between about 0.50 and 5.0 grams per pound of oat material and preferably about 2.15 grams per pound of oat material.

By increasing the glucoamylase concentration, it is possible to attain the higher glucose levels required for taste in a shorter time and reduce or eliminate off-flavors formed during the longer hold times normally employed for the glucoamylase.

The rate of glucose formation using the one-step process of the present invention was compared to the rate of glucose formation using a two-step process where the alpha-amylase reaction is done first followed by the glucoamylase reaction. The results of this study are reported in FIG. 1. Three comparative processes were evaluated: Gluco 1X used glucoamylase at 1 times the conventional concentration. Gluco 2.5X used glucoamylase at 2.5 times the conventional concentration. Gluco 5X used glucoamylase at 5 times the conventional concentration.

The higher initial glucose concentrations in the comparative materials results from the generation of some glucose during the alpha-amylase reaction. Using the process of the present invention, the rate of glucose formation is significantly higher immediately and in one-half the time. Using the one-step procedure of the present invention results in a significant reduction in the total processing time, which not only reduces the processing costs but also reduces the off-flavors generated by prolonged exposure of the oat-based functional syrup to increased temperatures.

After the syrup product obtains a desired degree of sweetness, the syrup product is cooled to a temperature of approximately 10° C. The syrup product is clean and bland with no off-flavors. If it is desired to increase the fructose concentration in the oat-based functional syrup, the oat-based functional syrup may be subjected to an isomerization step using techniques that are conventionally known in the art.

As noted above, producing an oat-based functional syrup that has a nearly white color enhances the ability to incorporate the oat-based functional syrup into a variety of products. It has been found that subjecting the oat-based functional syrup to clarification lightens the color of the oat-based functional syrup so that the oat-based functional syrup is nearly white.

Depending on the product that is to be made with the oat-based functional syrup, the oat-based functional syrup may be diluted with water to have a consistency (about 14 percent by weight solids) that is similar to milk prior to performing clarification.

During the clarification step, the oat-based functional syrup is run through a simple milk clarifier, which is also known as a cream separator. The oat-based functional syrup exiting the milk clarifier is almost white in color. The extent to which the color of the oat-based functional syrup is lightened depends upon the residence time of the oat-based functional syrup in the milk clarifier. A longer residence time results in a paler, weaker colored product similar to skim milk.

The length of the clarification process also depends on the G force used in the clarifier. For example, subjecting the oat-based functional syrup to a G force of about 2,000 G for less than one minute removes a significant amount of suspended material. Higher G forces (4,500 G) result a paler, lighter colored product. The amount of force imparted in a conventional clarifier is typically between 7,000 and 8,500 G.

Product resulting from the clarification step is largely improved in color. A white drink or frozen dessert is highly attractive to the consumer and an advantage in the market. A white product also is easier to color. Some improvement in taste is also apparent, especially in a diluted or milk formula (14 percent by weight solids). However, it is been found that extensive clarification of the syrup intended for frozen desserts removes some of the desired texture qualities—smoothness and mouthfeel—and is not recommended.

The oat-based functional syrup may be used to prepare food products and beverages. The oat-based functional syrup may then be flavored as desired using flavoring ingredients that are known in the art. For example, vanilla or cocoa may be added to the oat-based function syrup to produce vanilla or chocolate flavored non-dairy frozen confection. It may also be desirable to add a dairy- or cream-like flavor to the oat-based functional syrup so that the non-dairy frozen confection tastes more similar to ice cream.

The flavor of the oat-based functional syrup may be enhanced by the addition of a small concentration of a flavor enhancer. Various flavor enhancers are known in the art and are selected based upon the particular flavoring ingredients that are used in the non-dairy frozen confection. It is also possible to enhance the flavor of the food products and beverages made from the oat-based functional syrup by adding salt in a concentration of up to 1 percent by weight and preferably approximately 0.35 percent by weight of the oat-based functional syrup. It is believed that adding salt to the oat-based functional syrup after the oat-based functional syrup is formed minimizes off-flavors resulting from the addition of the salt while the oat-based functional syrup is being prepared.

After the oat-based functional syrup is flavored, the oat-based functional syrup may be frozen to produce a non-dairy frozen confection. The freezing is accomplished using processes and machines that are conventionally used to produce soft-serve or hard-pack prior art frozen confections.

The non-dairy frozen confection surprisingly exhibits desirable functional characteristics of a frozen confection but does not require the use of exogenous sweeteners, stabilizers, emulsifiers, or proteins to produce the desirable functional characteristics. For example, the sweetness of the non-dairy frozen confection results from the glucose and alternatively fructose produced during the saccharification and glucose isomerization steps.

The non-dairy frozen confection exhibits desirable viscosity characteristics without the addition of exogenous sweeteners, stabilizers, emulsifiers, or proteins. The desirable viscosity characteristics result from the naturally occurring fiber and gums in the starch sources. In particular, the texture of the non-dairy frozen confection depends upon beta-glucan being naturally present at a level sufficient for beta-glucan to act both as a stabilizer and texturizing agent in the oat-based functional syrup. Further functional contributions to the non-dairy frozen confection are also provided by starch degradation products.

Additionally, the non-dairy frozen confection made from the oat-based functional syrup exhibits texture and mouthfeel that are similar to ice cream, frozen yogurt, and other similar frozen confections. It is believed that the naturally occurring fat, protein, and fiber in oats result in the non-dairy frozen confection exhibiting a smooth mouthfeel characteristic. Furthermore, the oat-based functional syrup does not require emulsification or homogenization to produce the smooth mouthfeel characteristic in the non-dairy frozen confection.

A person of ordinary skill in the art would also appreciate that the oat-based functional syrup of the present invention could be used to formulate other foods and beverages. For example, the oat-based functional syrup may be used to produce shakes, malts, and puddings. The oat-based functional syrup may also be incorporated into carbohydrate-loading beverages that take advantage of the same physical and nutritional characteristics that make the oat-based functional syrup of the present invention useful for frozen confections.

Still another aspect of the present invention relates to fruit and oat drinks that are made from the oat syrup prepared according to the present invention. The fruit and oat drinks are made by blending the oat syrup with a concentrated fruit juice or pureed fruit. While it is typically not necessary to add other materials to the fruit and oat drink to enhance the sweetness of the fruit and oat drink, a person of ordinary skill in the art will appreciate that it is possible to add a variety of sweeteners such as sugar to balance the sweetness of the fruit and oat drink.

A person of ordinary skill in the art will appreciate that a variety of fruits may be used in formulating the fruit and oat drink. Examples of suitable fruits that may be used in the fruit and oat drink include oranges, strawberries, peaches, pears, apples, mango, or combinations thereof.

A person of ordinary skill in the art would appreciate that additives, such as pectin, gums, emulsifiers such as mono- and di-glycerides, bodying agents including cyclodextrose and maltodextrins, and the like, may be added to change the texture of food products and beverages made primarily from the oat-based functional syrup. However, such additives are unnecessary for the production of satisfactory food products and beverages, and would tend to lessen the consumer appeal of a product free of additives.

The product and method of the present invention are described in the following examples. These examples are provided as an illustration of the invention and are not intended to limit the invention.

EXAMPLE 1

A batch of oat syrup was prepared using a 26 percent concentration of fine oat flour and water. Prior to use the fine oat flour was passed through a U.S. #100 mesh sieve. Alpha-amylase (Genencor SPEZYME LT-75) was added at a concentration of about 0.7 grams per pound of oat flour. Glucoamylase was added at a concentration of about 2 grams per pound of oat flour.

Over a period of approximately 20 to 30 minutes, the slurry was heated to approximately 68° C. During this heating process, the slurry is thoroughly agitated. Once attaining the target temperature of approximately 68° C., the slurry was maintained at the target temperature for approximately 2.5 hours to convert the slurry into the syrup product. Thereafter, the oat-based functional syrup was cooled to a temperature of between about 10° C. and 16° C.

The DE (dextrose equivalent) of the oat-based functional syrup was approximately 60 + and the oat-based functional syrup had a glucose level of between about 14 and 16 percent by weight. The oat-based functional syrup was substantially free of any cereal-type flavors and had no off-flavors or aftertaste.

EXAMPLE 2

The oat-based functional syrup was placed into a conventional soft serve machine to prepare a frozen confection from the oat-based frozen confection. The soft serve machine was operated at conditions that are similar to the conditions used with conventional ice cream or yogurt. The substantially frozen oat-based functional syrup was then dispensed from the soft serve machine.

The oat-based functional syrup resulted in a high quality soft serve product, exhibiting excellent texture, superior meltdown and expected sweetness level. The frozen soft serve product was virtually free of any cereal-type flavors and had no off-flavors or aftertaste.

EXAMPLE 3

The oat-based function syrup was prepared into a hard pack form using a process that was substantially identical to the process used for preparing hard pack ice cream. The air overrun used in preparing the hard pack product was approximately 60 percent.

The oat-based functional syrup resulted in a high quality hard pack product, exhibiting excellent texture, superior meltdown and expected sweetness level. The frozen hard pack product was virtually free of any cereal-type flavors and had no off-flavors or aftertaste.

EXAMPLE 4

An orange-oat drink was prepared using the concepts of the present invention. As an initial step the oat syrup produced in Example 1 was passed through a milk clarifier. A mixture was prepared from approximately 1,000 grams of clarified oat syrup, approximately 240 grams of concentrated orange juice, and approximately 14 grams of all natural granulated sugar.

The mixture was blended in a conventional blender until the mixture was substantially homogeneous. The orange-oat drink thereby produced exhibited an orange to deep yellow color. The orange-oat drink had a tangy, orange flavor with a mild oat-flavor overtone. The texture of the orange-oat drink was very smooth. The orange-oat drink exhibited a moderate viscosity that was thicker than whole milk and less thick than a malt. When allowed to stand for an extended period of time, the components of the orange-oat drink did not separate to any notable extent.

EXAMPLE 5

The orange-oat drink prepared in Example 4 was placed into a conventional soft serve machine to prepare a frozen confection from the orange-oat drink. The soft serve machine was operated at conditions that are similar to the conditions used with conventional ice cream or yogurt. The substantially frozen orange-oat mixture was dispensed from the soft serve machine.

The orange-oat mixture resulted in a high quality soft serve product, exhibiting excellent texture, superior meltdown and expected sweetness level. The frozen soft serve product was virtually free of any cereal-type flavors and had no off-flavors or aftertaste.

EXAMPLE 6

A strawberry-oat drink was prepared using the concepts of the present invention. As an initial step the oat syrup produced in Example 1 was passed through a milk clarifier. Semi-frozen strawberries were pureed with hand-held type mixer for between about 5 and 7 minutes. A mixture was then prepared from approximately 1,000 grams of clarified oat syrup and approximately 236 grams of pureed strawberries.

The mixture was blended in a conventional blender until the mixture was substantially homogeneous. The blending was done in a three-step process. The mixture was blended at a medium speed for between about 1 and 2 minutes. The mixture was then blended on a high speed for between about 4 and 5 minutes. Next, the mixture was blended on a medium speed for between 1 and 2 minutes.

The strawberry-oat drink thereby produced exhibited a light red to pink color with fruit pieces and seeds apparent. The strawberry-oat drink had a strawberry flavor with a mild oat-flavor overtone. The texture of the strawberry-oat drink was very smooth with a contribution of the fruit yielding some diversity texture and thickness. The strawberry-oat drink exhibited a moderate viscosity that was thicker than whole milk and less thick than a malt. When allowed to stand for an extended period of time, the components of the strawberry-oat drink did not separate to any notable extent.

Although the present invention has been described with reference to preferred embodiments, workers skilled in the art will recognize that changes may be made in form and detail without departing from the spirit and scope of the invention.

What is claimed is:

1. A process for forming an oat-based functional syrup, the process comprising the steps of:
   milling an oat material to produce a base formulation;
   separating material having a granulation of more than U.S. #100 mesh from the base formulation, wherein separating reduces a bran concentration in the base formulation by more than 50 percent by weight;
   blending the base formulation with water to form a slurry;
   mixing an effective amount of an alpha-amylase enzyme into the slurry;
   mixing an effective amount of a glucoamylase enzyme into the slurry; and
   cooking the slurry to convert the slurry into a syrup, wherein the syrup is substantially flavorless.

2. The process of claim 1, and further comprising passing the syrup through a clarifier, wherein the clarified syrup has a nearly white color.

3. The process of claim 1, wherein material having a granulation of more than U.S. #250 mesh is separated from the base formulation.

4. The process of claim 1, wherein cooking the slurry comprises: heating the slurry to a target temperature of less than about 70° C.; and maintaining the slurry at the target temperature for approximately 2 hours to convert the slurry into the syrup.

5. The process of claim 4, wherein the target temperature is between 65° C. and 70° C.

6. The process of claim 4, and further comprising filtering the syrup to remove unconverted portions of the slurry.

7. The process of claim 1, wherein the alpha-amylase enzyme is added at a rate of between about 0.50 and 1.25 grams per pound of oat material.

8. The process of claim 1, wherein the glucoamylase is added at a rate of between about 0.5 and 5.0 grams per pound of the oat material.

9. The process of claim 1, wherein water is added to the slurry to produce a solids level of between about 25 and 33 percent on a dry matter basis.

10. The process of claim 1, wherein cooking lasts between about 1 and 3 hours.

11. The process of claim 1, wherein the syrup exhibits selected sweetness, texture, and mouthfeel characteristics while being devoid of exogenous sweeteners, stabilizers, emulsifiers, or proteins.

12. The process of claim 1, and further comprising mixing additional starch sources into the base formulation, wherein the starch sources comprise corn flour, wheat flour, rice flour, barley flour, potato flour, or combinations thereof.

13. The process of claim 1, and further comprising freezing the syrup to form a non-dairy frozen confection.

14. The process of claim 1, and further comprising mixing the syrup with fruit to produce a drink or a non-dairy frozen confection.

15. The process of claim 14, and further comprising pureeing or juicing the fruit.

16. A process for forming an oat-based functional syrup, the process comprising the steps of:

mixing a major amount of an oat material or waxy barley hybrid flour with a minor amount of a starch source to form a base formulation, wherein the starch source is oat flour, corn flour, wheat flour, rice flour, barley flour, potato flour, or combinations thereof;

milling the base formulation;

separating material having a granulation of more than U.S. #100 mesh from the base formulation, wherein separating reduces a bran concentration in the base formulation by more than 50 percent by weight;

blending the base formulation with water to form a slurry;

mixing an effective amount of an alpha-amylase enzyme into the slurry;

mixing an effective amount of a glucoamylase enzyme into the slurry; and cooking the slurry to convert the slurry into a syrup, wherein the syrup is substantially flavorless and has a nearly white color.

17. The process of claim 16, and further comprising passing the syrup through a clarifier, wherein the clarified syrup has a nearly white color.

18. The process of claim 16, wherein material having a granulation of more than U.S. #250 mesh is separated from the base formulation.

19. The process of claim 16, wherein cooking the slurry comprises: heating the slurry to a target temperature of less than about 70° C.; and maintaining the slurry at the target temperature for approximately 1 hour to convert the slurry into the syrup.

20. The process of claim 19, wherein the target temperature is between 65° C. and 70° C.

21. The process of claim 19, and further comprising filtering the syrup to remove unconverted portions of the slurry.

22. The process of claim 16, wherein the alpha-amylase enzyme is added at a rate of between about 0.50 and 1.25 grams per pound of oat material.

23. The process of claim 16, wherein the glucoamylase is added at a rate of between about 0.5 and 5.0 grams per pound of the oat material.

24. The process of claim 16, wherein cooking lasts between about 1 and 2 hours.

25. The process of claim 16, wherein the syrup exhibits selected sweetness, texture, and mouthfeel characteristics while being devoid of exogenous sweeteners, stabilizers, emulsifiers, or proteins.

26. A process for forming an oat-based functional syrup, the process consisting essentially of the steps of:

milling an oat material to produce a base formulation;

separating material having a granulation of more than U.S. #100 mesh from the base formulation;

blending the base formulation with water to form a slurry;

mixing an effective amount of an alpha-amylase enzyme into the slurry;

mixing an effective amount of a glucoamylase enzyme into the slurry; and cooking the slurry to convert the slurry into a syrup, wherein the syrup is substantially flavorless.

27. The process of claim 26, and further comprising passing the syrup through a clarifier, wherein the clarified syrup has a nearly white color.

\* \* \* \* \*

UNITED STATES PATENT AND TRADEMARK OFFICE
CERTIFICATE OF CORRECTION

PATENT NO. : 6,685,974 B2  Page 1 of 1
DATED : February 3, 2004
INVENTOR(S) : Whalen It is certified that error appears in the above-identified patent and that said Letters Patent is hereby corrected as shown below:

Drawings,
Please delete erroneous Figure 1, " 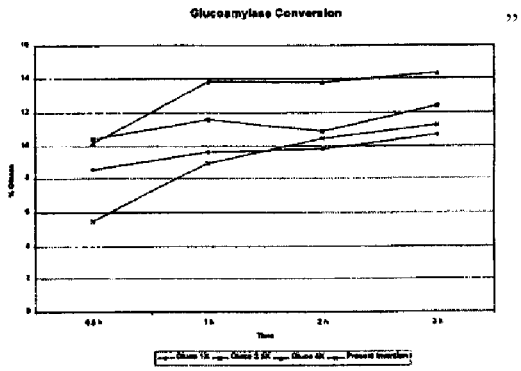 "

and insert correct Figure 1, -- 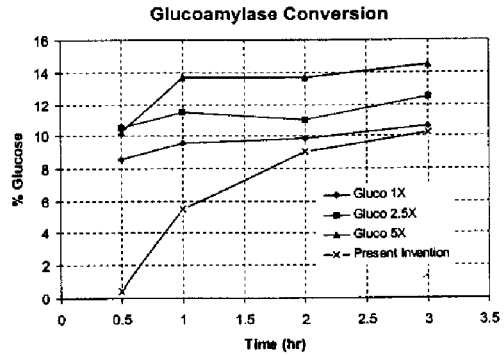 --

Signed and Sealed this

Eighth Day of February, 2005

JON W. DUDAS
*Director of the United States Patent and Trademark Office*